United States Patent [19]

Nedelec et al.

[11] 4,175,136
[45] Nov. 20, 1979

[54] N-PHENETHYL-N-PROPYL-3,4-DIHYDROX-YPHENETHYLAMINES AND SALTS THEREOF

[75] Inventors: Lucien Nédélec, Le Raincy; Daniel Frechet, Paris; Claude Dumont, Nogent-sur-Marne, all of France

[73] Assignee: Roussel UCLAF, Paris, France

[21] Appl. No.: 905,535

[22] Filed: May 12, 1978

Related U.S. Application Data

[63] Continuation of Ser. No. 744,514, Nov. 24, 1976, abandoned.

[51] Int. Cl.² .................. A01N 9/20; A01N 9/24; C07C 91/32
[52] U.S. Cl. .................. 424/330; 260/501.18; 260/501.19; 260/570.8 R; 424/316
[58] Field of Search .................. 260/570.8 R, 501.18, 260/501.19; 424/316, 330

[56] References Cited

U.S. PATENT DOCUMENTS 2,276,618   3/1942   Kulz .................. 260/570.8

FOREIGN PATENT DOCUMENTS 64503   9/1949   Netherlands .................. 260/570.8

OTHER PUBLICATIONS

Kurlz et al., "Beriehte", vol. 72 B, pp. 2161–2167 (1939).

Primary Examiner—Robert V. Hines
Attorney, Agent, or Firm—Hammond & Littell

[57] ABSTRACT

N-phenethyl-N-propyl-3,4-dihydroxyphenethylamine and its non-toxic, pharmaceutically acceptable acid addition salts possessing dopaminergic properties.

7 Claims, No Drawings

N-PHENETHYL-N-PROPYL-3,4-DIHYDROXY-PHENETHYLAMINES AND SALTS THEREOF

This is a continuation of Ser. No. 744,514, filed Nov. 24, 1976 and now abandoned.

STATE OF THE ART

French Pat. Nos. 891,931 and No. 903,296 disclose aliphatic aromatic secondary and tertiary amines of the formula

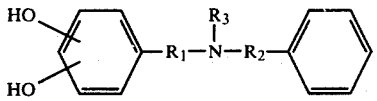

wherein $R_1$ and $R_2$ are branched or straight chain alkyl or alkylene groups and $R_3$ is hydrogen or branched or straight chain alkyl and alkylene groups which possess analgesic properties.

OBJECTS OF THE INVENTION

It is an object of the invention to provide N-phenethyl-N-propyl-3,4-dihydroxyphenethylamine and its non-toxic, pharmaceutically acceptable acid addition salts and a process for their preparation.

It is another object of the invention to provide novel dopaminergic compositions and to a novel method of treating the symptoms of Parkinson disease.

These and other objects and advantages of the invention will become obvious from the following detailed description.

THE INVENTION

The novel products of the invention are N-phenethyl-N-propyl-3,4-dihydroxyphenethylamine of the formula

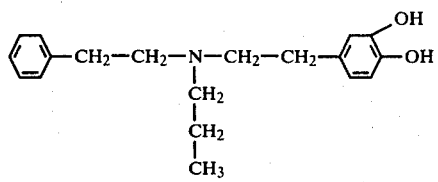

and its non-toxic, pharmaceutically acceptable acid addition salts.

Examples of suitable acids for the formation of the non-toxic, pharmaceutically acceptable acid addition salts are inorganic acids such as hydrochloric acid, hydrobromic acid, hydriodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic acid, aspartic acid, alkanesulfonic acids like methane sulfonic acid and arylsulfonic acids like benzene sulfonic acid. Particularly preferred is the hydrochloride salt.

The process of the invention for producing the novel products comprises reacting a propyl halide of the formula

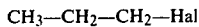

wherein Hal is chlorine, bromine or iodine with an amine of the formula

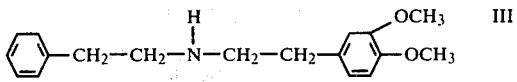

in the presence of an alkaline agent to form a compound of the formula

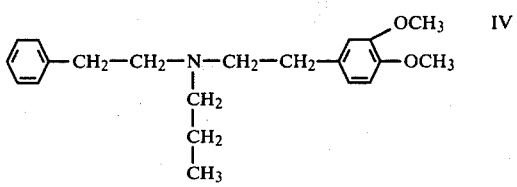

and hydrolyzing the latter to form the compound of formula I which may be salified, if desired.

The reaction of the propyl halide of formula II with the amine of formula III is preferably effected in an anhydrous organic solvent such as acetone in the presence of an alkaline agent such as alkali metal carbonates like potassium carbonate and the hydrolysis of the compound of formula IV is preferably effected with a solution of concentrated hydrobromic acid, at the reflux for 1 to 5 hours. The base of formula I may be salified by known methods by reacting approximately stoichiometric properties of an appropriate inorganic or organic acid and the base of formula I.

The dopaminergic compositions are comprised of a dopaminergically effective amount of at least one compound selected from the group consisting of N-phenethyl-N-propyl-3,4-dihydrophenethylamine and its non-toxic, pharmaceutically acceptable acid addition salts and an inert pharmaceutical carrier. The compositions may be in the form of tablets, dragees, gelules, granules, suspositories and injectable solutions or suspensions.

Examples of suitable excipients or carriers are talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, dispersants or emulsifiers.

The compositions, due to their remarkable dopaminergic properties are useful for the treatment of neurologic syndroms of extrapyramidal origins such as the syndroms of Parkinson disease, of post-encephalitic parkinsonian syndroms of parkinsonian syndroms of arteriosclerous origin or toxic etiology.

The novel method of the invention for inducing dopaminergic activity in warm-blooded animals, including humans, comprises administering to warm-blooded animals a dopaminergically effective amount of N-phenethyl-N-propyl-3,4-dihydroxyphenethylamine or its non-toxic, pharmaceutically acceptable acid addition salt. The compounds may be administered orally, rectally or parenterally and the usual daily dose is 0.2 to 4 mg/kg depending on the specific compound and treatment.

The hydrochloride of the compound of formula III is described in J.A.C.S., Vol. 53 (1931), p. 2192–2200.

In the following examples there are described several preferred embodiments to illustrate the invention. However, it should be understood that the invention is not intended to be limited to the specific embodiments.

EXAMPLE 1

N-phenethyl-N-propyl-3,4-dihydroxyphenethylamine hydrochloride

STEP A:
N-phenethyl-3,4-dimethoxyphenethylamine

A mixture of 10 g of homoveratrylamine and 12 g of β-phenethyl bromide was stirred for 15 minutes at 125° C. in a bath and after cooling the mixture to 60° C., 30 ml of acetone were added. The mixture was iced and vacuum filtered and the recovered precipitate was dissolved in 250 ml of methanol. The solution was concentrated to 50 ml and 400 ml of ethyl acetate were added thereto. The mixture was concentrated to 200 ml, was iced and vacuum filtered to obtain 12.5 g of raw product. The latter was crystallized from isopropanol to obtain 9 g of N-phenethyl-3,4-dimethoxyphenethylamine hydrobromide in the form of colorless crystals melting at 180° C.

25 g of the latter hydrobromide were dissolved in 250 ml of hot water and the solution was cooled to 0° C. and made alkaline with 40 ml of 2 N sodium hydroxide. The mixture was extracted 3 times with 100 ml of ethyl acetate and the organic extracts were washed with water until the wash water had a pH of 7 to 8. The extracts were dried over sodium sulfate, were filtered and evaporated to dryness under reduced pressure to obtain 19 g of N-phenethyl-3,4-dimethoxyphenethylamine.

STEP B:
N-phenethyl-N-propyl-3,4-dimethoxyphenethylamine

A solution of 8 g of N-phenethyl-3,4-dimethoxyphenethylamine, 8 g of anhydrous potassium carbonate, 11 ml of propyl iodide and 80 ml of acetone was refluxed for 6 hours and the mixture was filtered. The filtrate was evaporated to dryness and the residue was taken up in 50 ml of water. The solution was extracted with methylene chloride and the organic extracts were washed with water, dried over magnesium sulfate, filtered and evaporated to dryness to obtain 9.37 g of raw N-phenethyl-N-propyl-3,4-dimethoxyphenethylamine in the form of an oil which was used as is for the next step.

STEP C:
N-phenethyl-N-propyl-3,4-dihydroxyphenethylamine hydrochloride

A solution of 9.37 g of the product of Step B in 90 ml of 48% hydrobromic acid was refluxed for 3 hours under a nitrogen atmosphere and was then evaporated to dryness. The residue was taken up in 50 ml of ammonium hydroxide solution and the solution was extracted with methylene chloride. The organic extracts were washed with water, dried over magnesium sulfate, filtered and evaporated to dryness to obtain 8.1 g of N-phenethyl-N-propyl-3,4-dihydroxyphenethylamine in the form of a reddish oil.

A solution of 8.1 g of the latter product in 80 ml of acetone was admixed with 120 ml of a solution of 0.5 N hydrochloric acid in ethyl acetate and the mixture was evaporated to dryness. The residue was dissolved in a refluxing mixture of 40 ml of acetone and 4 ml of ethyl acetate and the mixture was iced and vacuum filtered. The recovered precipitate was washed with methyl ethyl ketone to obtain 5.5 g of raw hydrochloride which were dissolved in a mixture of 10 ml of methanol and 200 ml of methyl ethyl ketone. The solution was concentrated to 50 ml and stood at 25° C. for 2 hours after which it was vacuum filtered. The recovered precipitate was washed with methyl ethyl ketone and was dried under reduced pressure to obtain 4.5 g of N-phenethyl-N-propyl-3,4-dihydroxyphenethylamine hydrochloride in the form of colorless crystals melting at 145° C.

Analysis: $C_{19}H_{25}NO_2 \cdot HCl$; molecular weight=335.87. Calculated: %C, 67.94; %H, 7.80; %Cl, 10.56; %N, 4.17. Found: %C, 68.1; %H, 7.9; %Cl, 10.7; %N, 4.0.

EXAMPLE 2

Tablets were prepared containing 50 mg of N-phenethyl-N-propyl-3,4-dihydroxyphenethylamine hydrochloride and an excipient of lactose, starch, talc and magnesium stearate.

PHARMACOLOGICAL STUDY

A. Antagonism to reserpinic rigidity

The antagonism of the compounds against reserpinic rigidity was studied in rats using the technique of Jurna I: Arch. Pharmak. Exp. Path., Vol. 260 (1968), p. 80–88. The test consisted of recording the electromyogram (EMG) with electrodes placed on the muscles of the anterior loge of one of the hind foot of the rats provoked by a dorsiflexion of the foot. A dose of 10 mg/kg of reserpine was administered intraveinously and 30 minutes later when the muscle hypertonicity was maximum, the tested product was administered in the same fashion. The electromyographic responses obtained before and after the latter treatment were compared for intensity and duration and the inhibition observed showed the antagonism exercised by the test product against rigidity provoked by reserpine. Under these test conditions, the product of Example 1 showed antagonistic activity to reserpinic rigidity at a dose of 10 mg/kg.

B. Behavior after unilateral injury of nigrostriatal bundle

Among the animals having undergone a unilateral lesion of nigrostriatal bundle, the substances, having a dopaminergic activity induce a rotating behavior. The animals were male rats weighing about 250 g and female mice weighing about 22 g. The lesion was effected in test (a) in the right striatum of the male rats with a 2 mA anodic current for a duration of 30 seconds [Anden et al, Acta. Pharmacol. Toxicol., Vol. 24 (1966), p. 263–274]. The tested compounds were administered intraperitoneally to groups of 6 animals and they were individually placed in a rotometer which counted the number of rotations of each animal in two directions. Each test was continued for 1½ hours.

In test (b) with the male rats, lesion was effected in the substantia nigra of each rat with 6-hydroxydopamine monohydrochloride at a dose of 20 μg per 4 μl of physiological serum containing 0.2 mg/ml of ascorbic acid by the method of Ungerstedt [Acta. Physiol. Scand., (1971) a, supp. 367, p. 69–93] and the same conditions as in (a) were used.

In test (c) with female mice, a lesion of the striatum was effected with a hypodermic needle with a diameter of 0.5 mm by aspiration under vacuum for 5 seconds with the method of Lotti [Life Science, Vol. 10 (1971) I, p. 781–789]. The tested compounds were intraperitoneally administered and the mice were observed for an hour to determine the number of mice showing rotation movements.

Under these conditions, the compound of Example 1 showed ipsilateral rotations at a dose of 10 mg/kg in test (a) and contralateral rotations at a dose of 2 mg/kg in test (b). At a dose of 50 mg/kg in test (c), the only experiment with the animals having been subjected to a lesion of type (c), the compound of Example 1 exhibited ipsilateral rotations. The results show that the compound possesses an important dopaminergic activity.

C. Acute toxicity

The 50% lethal dose (LD$_{50}$) was determined for the product of Example 1 after intraperitoneal administration to mice and the mortality was determined 48 hours after the administration of the test product. The LD$_{50}$ for product of Example 1 was about 75 mg/kg.

Various modifications of the products and methods of the invention may be made without departing from the spirit or scope thereof and it is to be understood that the invention is to be limited only as defined in the appended claims.

We claim:

1. A compound selected from the group consisting of N-phenethyl-N-propyl-3,4-dihydroxyphenethylamine of the formula

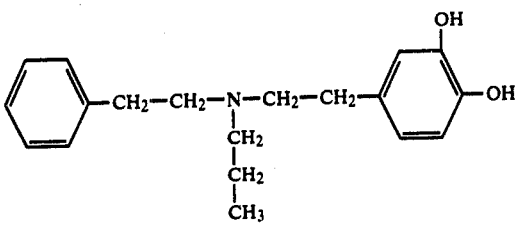

and its non-toxic, pharmaceutically acceptable acid addition salts.

2. A compound of claim 1 which is the hydrochloride salt of N-phenethyl-N-propyl-3,4-dihydroxyphenethylamine.

3. A dopaminergic composition comprising a dopaminergically effective amount of at least one compound of claim 1 and an inert pharmaceutical carrier.

4. A composition of claim 3 wherein the compound is the hydrochloride salt of N-phenethyl-N-propyl-3,4-dihydroxyphenethylamine.

5. A method of inducing dopaminergic activity in warm-blooded animals comprising administering to warm-blooded animals a dopaminergically effective amount of at least one compound of claim 1.

6. The method of claim 5 wherein the compound is the hydrochloride salt of N-phenethyl-N-propyl-3,4-dihydroxyphenethylamine.

7. The method of claim 6 wherein the compound is orally administered.

* * * * *

UNITED STATES PATENT AND TRADEMARK OFFICE
CERTIFICATE OF CORRECTION

PATENT NO. : 4,175,136
DATED : November 20, 1979
INVENTOR(S) : LUCIEN NEDELEC, DANIEL FRECHET and CLAUDE DUMONT It is certified that error appears in the above—identified patent and that said Letters Patent is hereby corrected as shown below:

On the title page, the following should be added:

--[30] Foreign Application Priority Data

Dec. 1, 1975 [FR] France................36683--.

Signed and Sealed this

Sixteenth Day of October 1984

[SEAL]

Attest:

Attesting Officer

GERALD J. MOSSINGHOFF

Commissioner of Patents and Trademarks